United States Patent [19]

Berry

[11] Patent Number: 5,306,300
[45] Date of Patent: Apr. 26, 1994

[54] TUBULAR DIGESTIVE SCREEN

[76] Inventor: H. Lee Berry, 4304 Evergreen La., #204, Annandale, Va. 22003

[21] Appl. No.: 948,498

[22] Filed: Sep. 22, 1992

[51] Int. Cl.⁵ .......................... A61F 2/02; A61F 2/04; A61F 2/54
[52] U.S. Cl. ...................................... 623/11; 623/12; 623/66
[58] Field of Search ............... 623/11, 12, 66; 604/43, 604/54, 93, 95

[56] References Cited

U.S. PATENT DOCUMENTS

| | | |
|---|---|---|
| 4,134,405 | 1/1979 | Smit . |
| 4,315,509 | 2/1982 | Smit . |
| 4,403,604 | 9/1983 | Wilkinson et al. . |
| 4,416,267 | 11/1983 | Garren et al. . |
| 4,501,264 | 2/1985 | Rockey . |

OTHER PUBLICATIONS

Berry, *Collagenous Fiber Patterns in the Submucosa of the Small Intestine of the Dog*, "The Anatomical Record" vol. 143, No. 2 Jun. 1962, pp. 107-116.

"Gray's Anatomy", 1974 pp. 905-911.
"Moss Suction Buster Decompression/Feeding Tubes".
Neher et al, *The Patch Clamp Technique*, "Scientific American" Mar. 1992, pp. 44-51.
Halmi, *Gastric Bypass for Massive Obesity*, "Obesity" Chapter 20 pp. 388-394.
Kral, *Surgical Therapy*, "Obesity" Chapter 3, pp. 25-38.

*Primary Examiner*—Randall L. Green
*Assistant Examiner*—Dinh X. Nguyen
*Attorney, Agent, or Firm*—Stevens, Davis, Miller & Mosher

[57] ABSTRACT

A tubular digestive screen for use in controlling the caloric intake of persons having morbid obesity is disclosed. The screen is made up of a thin-walled membrane-like tube, which has a firm ring at the top of the tube, a funnel-shaped portion below the firm ring, a tubular portion of constant diameter beginning below the funnel-shaped portion, and a distal end of the tube having a brush. The screen can be inserted and maintained in the digestive system of a patient without the need for an anchoring chain within the tube.

4 Claims, 6 Drawing Sheets

TUBULAR DIGESTIVE SCREEN

The present invention relates to a tubular digestive screen for use in controlling caloric intake in persons having morbid obesity.

BACKGROUND OF THE INVENTION

Morbid obesity is a behavioral disorder which may render a person unable to lose weight by normal procedures. Morbid obesity is defined by Dorland's Medical Dictionary as "the condition of weighing two or three or more times the ideal weight; morbid obesity is often associated with serious and life threatening disorders." No pathology can be demonstrated in the stomach and small intestine in this eating disorder. The digestive system is normal. It is well established in the medical world that obesity of this magnitude lead to a much shorter than normal life span. There is severe strain on the heart, lungs and musculoskeletal systems, and threats to the general health comes from many directions.

For several decades, various bold and courageous surgeons have subjected a very limited number of patients having morbid obesity to surgical modifications, including:

1) Removing part of the stomach and rearranging the small bowel;
2) Stapling part of the stomach and rearranging the small bowel; and
3) Bypassing the stomach by rearranging the jejunum and making a pouch of the upper intestines. See for example, Halmi, *Gastric Bypass for Massive Obesity*, Chapter 20 of "Obesity", edited by Stunkard, pages 25-38; and Kral, *Surgical Therapy*, Chapter 3 of "Obesity" edited by Greenwood, pages 25-38.

Many of these procedures seemed encouraging and promising at the time but none of them resulted in happy, healthy patients recovering from morbid obesity. For one thing, all of these techniques are irreversible and commit the patient to suffer symptoms related to, for example, indigestion, poor vitamin assimilation, diarrhea, malnutrition and the like. The surgeon cannot rearrange these organs without danger to the patient.

DISCUSSION OF PRIOR ART

U.S. Pat. No. 4,134,405, to Smit, relates to a catheter and intestine tube. The catheter, as described therein, is used to insert the intestine tube thereof. The intestine tube is an extremely thin wall tube, made preferably of a plastic such as a silicone material. The tube is impervious and, therefore, can be used in the treatment of obesity. Within the thin wall tube is a semi-flexible chain, which assists in both insertion and anchoring of the tube, preventing twisting thereof. U.S. Pat. No. 4,315,509, also to Smit, is directed to an improvement in the device of U.S. Pat. No. 4,134,405. Except as discussed below, the disclosures of U.S. Pat. No. 4,134,405 and U.S. Pat. No. 4,315,509 are hereby incorporated by reference into the present application.

Although the Smit patents disclose that they can be used in the treatment of obesity or alcoholism, it would now be clear to one skilled in the art that the catheter and intestinal tube thereof would not work in this capacity and that some of the disclosure of the Smit patents is incorrect, as discussed as follows with reference to U.S. Pat. No. 4,134,405. Column 1, lines 16-23 discuss an example of the lining of such as tube. First, the present applicant notes that such a lining would not be effective in the treatment of ulcers, alcoholism and the like. Other more acceptable treatments have been found for these disorders. Additionally, Smit is incorrect in asserting that the presence of such a tube would stimulate the villi causing an increased absorption of food chemicals necessary for weight gain or for treating absorption-related deficiencies. The presence of a tube would not affect the amount of absorption necessary for weight gain; it would merely decrease the amount of food available for absorption.

Further, as will be clear to one skilled in the art, the intestinal tube of Smit could not be inserted as disclosed therein, and even if it were inserted, such tube would not have any practical utility in the treatment of obesity. Contrary to the assertions in Smit, such a tube cannot be inserted through the mouth, pharynx and esophagus into the stomach by the method described. As would be clear to one skilled in the art, the insertion of tubes into the lower stomach the duodenum, the jejunum and the ilium are within the provinces of a surgeon, and it will be necessary for a surgeon to insert an intestinal tube for use in the treatment of obesity. That is, a surgical procedure will certainly currently be necessary for the installation of such devices.

Additionally, the Smit patents require the presence of a semi-flexible, flat chain 34 within the tube to keep the tube stable and prevent twisting.

Another artificial membrane is discussed in Neher et al, *The Patch Clamo Technique*, Scientific American, pages 44-51 (March, 1992).

Therefore, nothing in the prior art discloses or suggests the present invention.

BRIEF DESCRIPTION OF THE INVENTION

An object of the present invention is to serve patients with a diagnosis of morbid obesity. People with morbid obesity are those whose lives are threatened because they cannot or will not limit their intake of large amounts of food and, particularly, large amounts of fat.

A second object of the present invention is to help any person who must lose weight for reasons of obesity-related health problems, such as hypertension, diabetes, or cardiac disease. Some people are very depressed and discouraged by even moderate obesity. The present invention may be simple enough to use and can be used for such less threatening situations as well.

These objectives are achieved by providing a nutritional screen which can be inserted by a surgeon that will interfere with the digestion, particularly of lipids (fats). The screen can be modified by simple surgical procedures and removed if unsatisfactory. The right length of tubular screen can eliminate the correct amounts of fats from being digested by the small intestine but allow sufficient digestion to occur to maintain adequate nourishment.

DETAILED DISCUSSION OF THE INVENTION AND THE PREFERRED EMBODIMENT THEREOF

Figure 1:
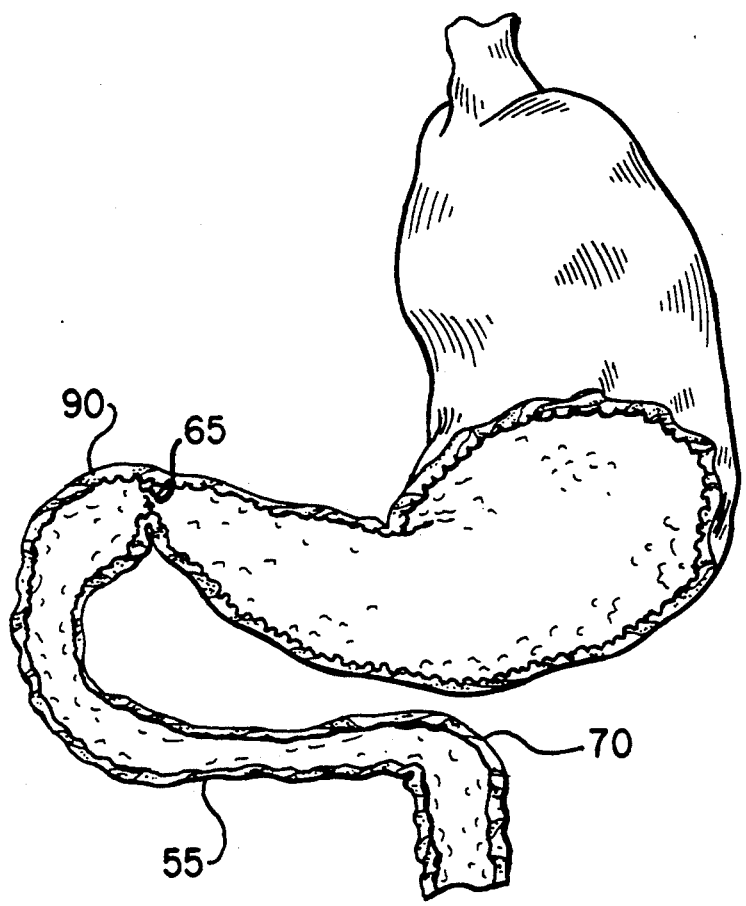
FIG. 1 shows a side view of the human digestive system prior to the insertion of the tubular digestive screen of the present invention.

The anatomy of the stomach is shown in, for example, *Gray's Anatomy*, pages 905–11 (1974), the disclosure of which is hereby incorporated by reference. The anatomy of the digestive system is shown in FIG. 1, in which 55 indicates the duodenum, 65 indicates the pyloric valve, 70 indicates the Ligament of Treitz and the beginning of the jejunum and 90 indicates the duodenal bulb.

Figure 2:
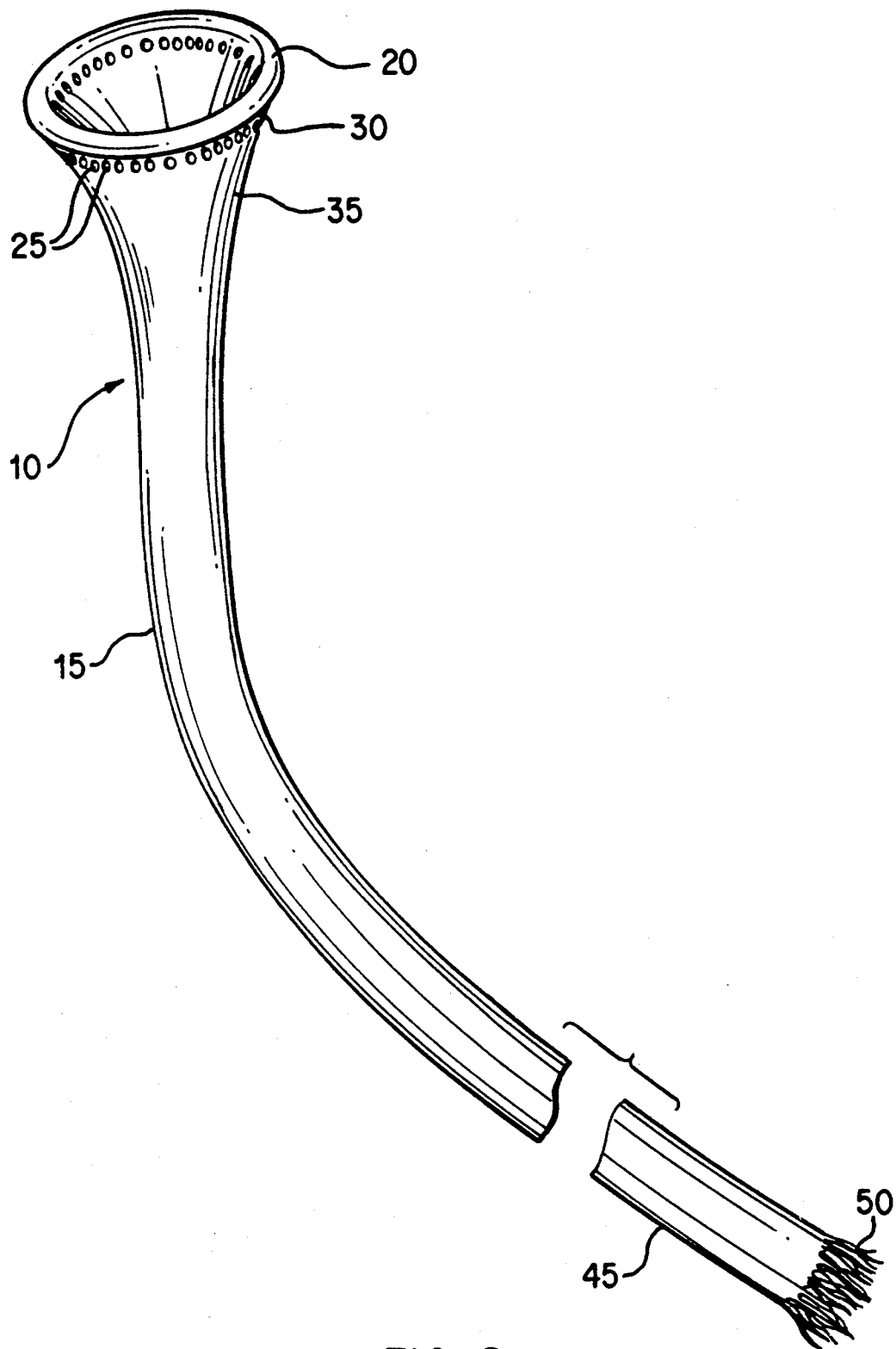
FIG. 2 shows a side view of one embodiment of the tubular digestive screen of the present invention.
Figure 5:
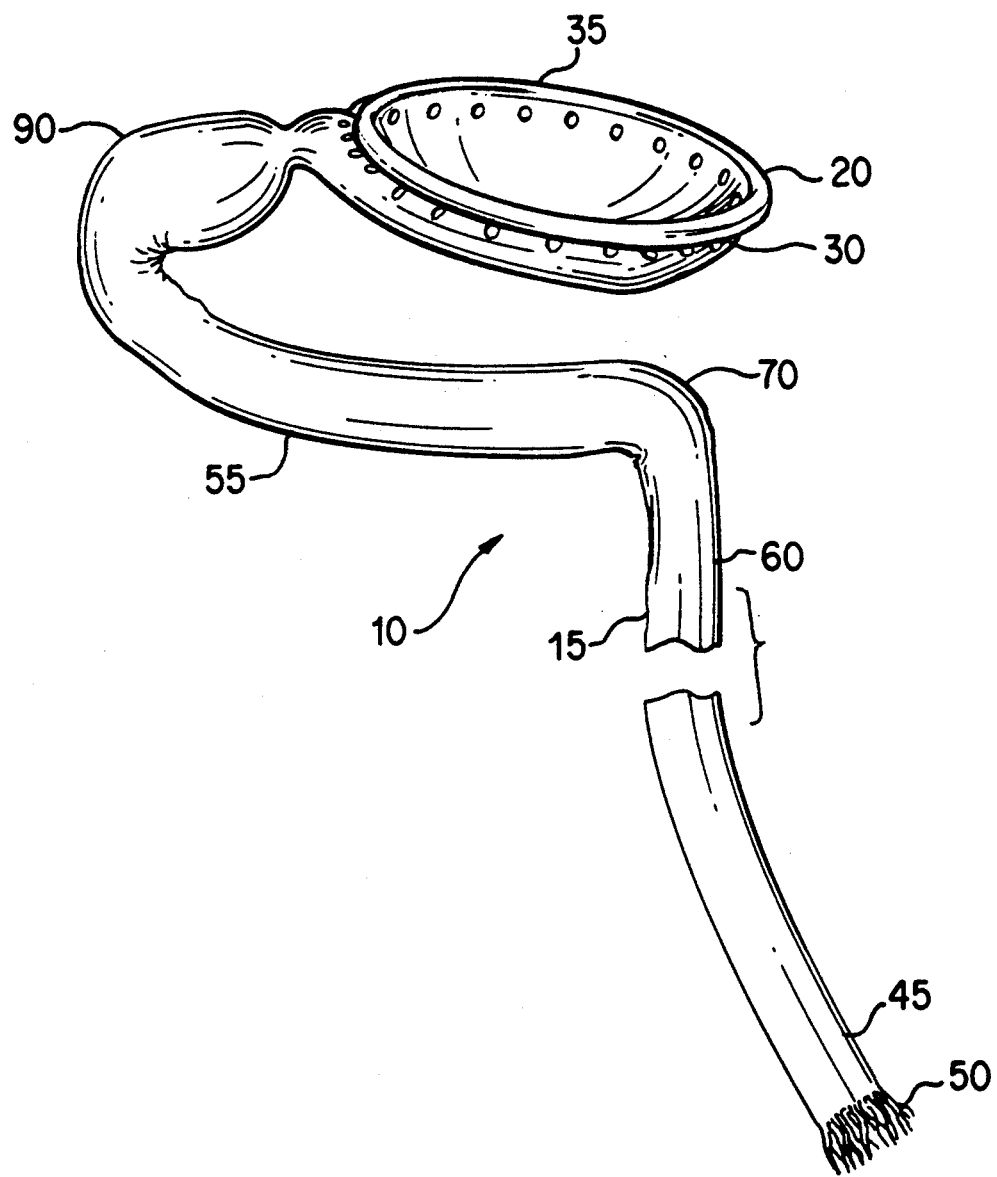
FIG. 5 shows another side view of the tubular digestive screen of FIG. 2.

The present invention relates to a tubular digestive screen 10, which is a thin-walled, membrane-like tube 15, as shown in FIG. 2. At the top of the tubular screen 10 is a firm ring 20 of rubber or plastic which is attached to the thin-walled tube 15. A soft, flexible flange (not shown) may also be present at the top of the tube 10. The first few inches of the tube 10 are funnel-shaped 35, after which the tube has a constant diameter of, for example, one inch. As is clear from FIGS. 5 and 6, the top portion of the tubular screen 10 can be pan shaped. The total length of the tube 15 will be determined by the needs of the patient in a manner which would be clear to one skilled in the art from the present disclosure. At the beginning of the funnel-shaped portion 35 of the tube 15 or anywhere around the opening of the tube 15, the tube 15 may be penetrated by small holes 25. Where there are concentrations of such holes that area can be described as a sieve 30. At various intervals the tube may be permeable, impermeable or semipermeable, made possible by the use of any variety of materials, from woven synthetics to plastics to membranes of latex or silicon. However, the tube cannot be of, for example, rubber, which will stretch as the tube empties. Therefore, the tube 15 of the present invention should be convoluted, as naturally in the body, and can be of any of a variety of materials other than rubber, as would be clear to one skilled in the art from the present disclosure. One such material which is usable in a tube of the present invention is a silicone material, such as Silastic TM (Dow Chemical's silicone elastomer materials and related products), which is a clear, seamless material designed for use in a variety of clinical and laboratory applications. The tube may have a delicate thin membrane (not shown) which limits secretions in the digestive tract due to the presence of the impermeable tube. In a second embodiment (not shown), the tube 15 may also have perforations to allow some interplay between the digestive tract and the food and thus allow some food adsorption. Artificial lipid membranes may be used in the obstruction of the tube to prevent the escape of lipids from the digestive stream, impeding digestion of fats as desired. At the distal end 45 of the tube 10, there may be vertical strips of the tube called the brush 50. The brush 50 provides an area of the tube that can freely respond to the peristaltic movement of the intestine in such a way as to exert a downward pull on the tube.

Figure 4:
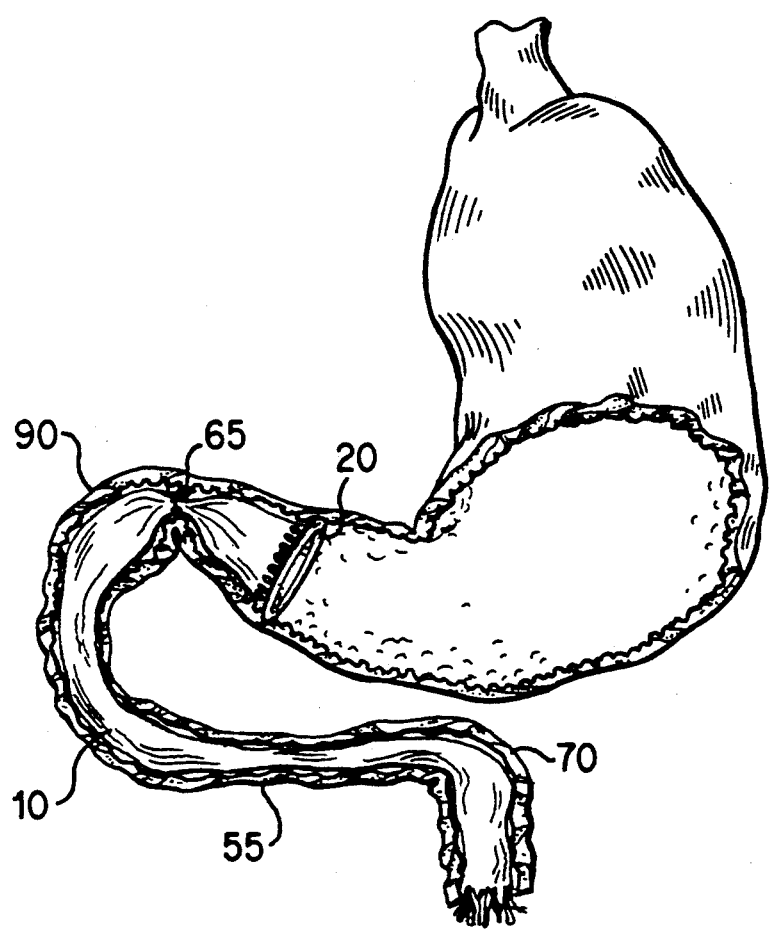
FIG. 4 shows a side view of one embodiment of the tubular digestive screen of the present invention after insertion into the digestive system.
Figure 6:
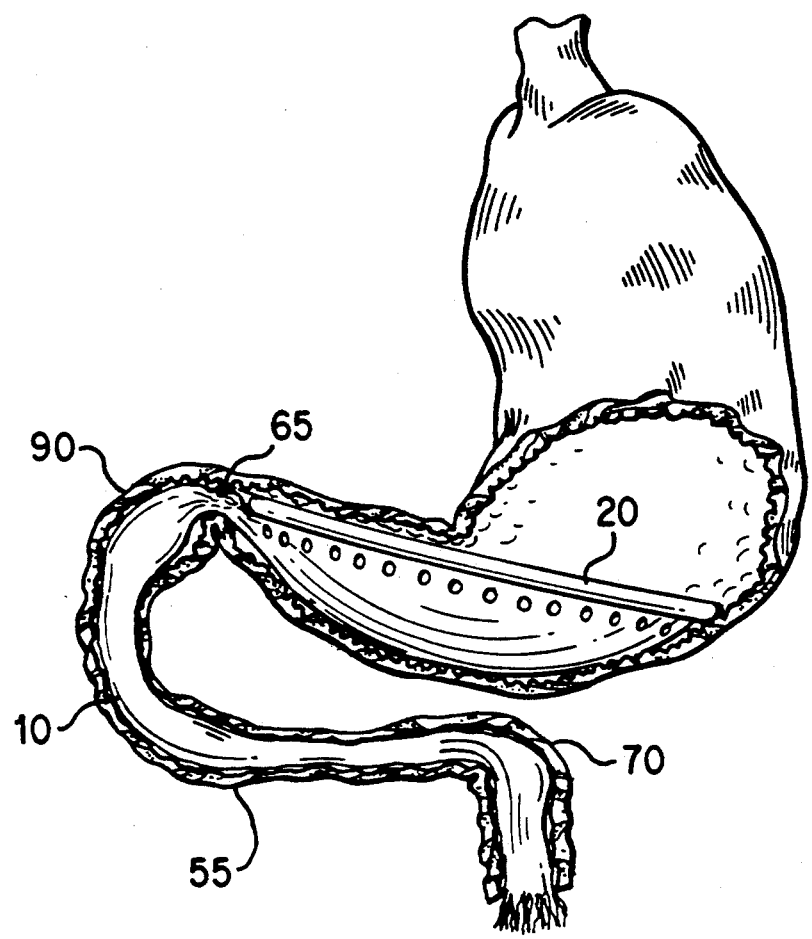
FIG. 6 shows a side view of another embodiment of the tubular digestive screen of the present invention after insertion into the digestive system.

The device is placed in the lower stomach by a surgeon or gastroenterologist, either surgically or by means of a tube passed down the esophagus, as shown in FIGS. 4 and 6. The firm ring 20 will be placed a few inches above the pylorus or pyloric valve 65, and the tubular screen 10 will be threaded through the pylorus 65, passing through the duodenum 55, the jejunum 60, and possibly into the ileum (not shown), depending on the needs of the patient. The ring size of the tube 15 will be selected by x-ray measurements and may be adapted somewhat to fit the patient. For example, the point selected for the firm ring 20 may be three inches above the beginning of the pylorus 65; the radiologist can measure that area and estimate the appropriate diameter of the ring. Peristaltic movements along the small bowel (not shown) and particularly the brush 50 will need to pull constantly downward to keep the tube 10 in place and the contents moving in the direction of the large bowel. Variations in the perforations in the tube 10 and the permeability of the material of which it is made will control the amount of nutrients allowed outside the tube and the amount of bile and pancreatic enzymes allowed inside the tube.

Such a tube is effective without the need for a semiflexible chain or the like within it. That is, the present invention is self-anchoring within the body, and no auxiliary anchoring device is necessary.

The use of the device as a digestive screen in the lower stomach and small bowel is shown in FIGS. 4 and 6 and further discussed as follows. The tubular digestive screen 10 hangs from the firm ring 20 in the lower stomach 70. The tube 15 is constantly pulled down by peristalsis along the tube 10 and is guided and also pulled down by the brush 50 at the distal end 45. Food will be mixed with gastric juices while in the stomach (not shown) and will receive an almost normal churning action of the stomach. Within the tube 10, the stomach contents will progress through the pylorus 65 and down the duodenum 55, borne along by the peristaltic movement of the gut. The food stream will thus be encouraged to flow in a normal way. The physician can, by varying the length of the tube and the perforations and materials of which it is constructed, control the extent to which bile and pancreatic enzymes remain outside the tube and nutrients remain inside the tube, thereby altering the process of digestion and controlling the amount of lipids, glucose, and proteins assimilated by the small bowel.

The physician will be able to retrieve the tube 10 to rest the bowel from time to time or to make adjustments to the tube and replace it as needed.

Figure 3:
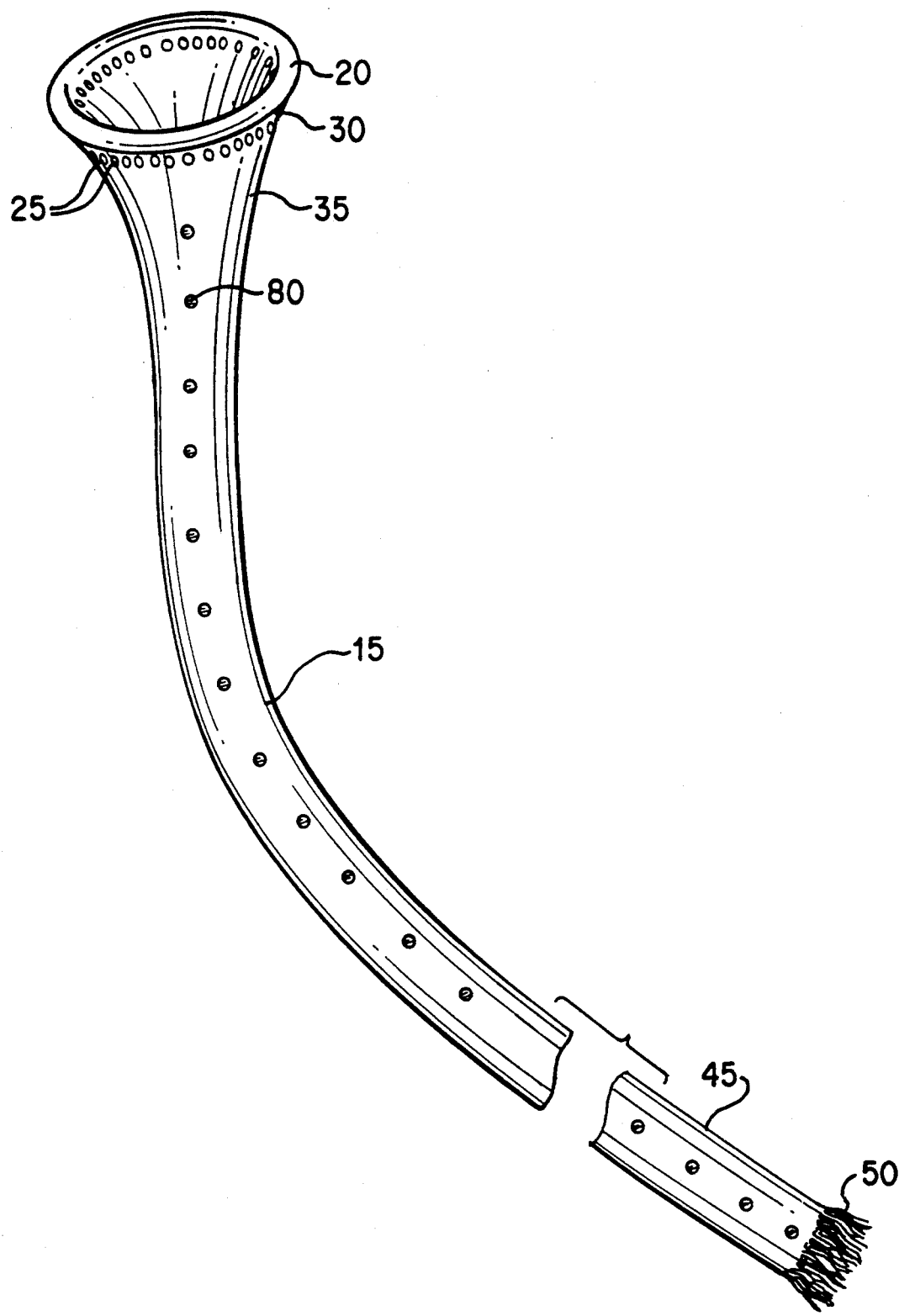
FIG. 3 shows a side view of another embodiment of the tubular digestive

The present invention also overcomes various problems known in the art when taking measurements of the small intestine. When measurements are taken of the small intestine, one must consider whether the gut is full or empty at the time, as well as other variables. For example, peristaltic waves constantly cause the length and diameter of the small intestine to vary, making it nearly impossible to duplicate the measurements taken. The method of measuring the small intestine of the present invention allows for more precise measurements, particularly of the length of the duodenum 55 and the jejunum 60. As shown in FIG. 3, into the wall of the tubular digestive screen 10 are incorporated a series of radio-opaque dots 80 beginning at the firm ring 20. The firm ring 20 will also be radio-opaque. Each of the dots 80 may be one sixteenth of an inch to one eighth of an inch in diameter. These dot markers 80 will be in one vertical plane and at a distance of, for example, one inch apart along the tube 15. The brush 50 at the end of the tube 10 will have such a marker at the end of each vertical part thereof. The Ligament of Treitz 90 is of value only as a marker. This ligament would be easily identified by the surgeon during the installation of the screen and can also be located by x-ray since it indicates where the duodenum ends and the jejunum begins. This point can also be easily located by the change in direction of the axis of the small bowel. From a clinical standpoint, the surgeon can easily find a precise location along the jejunum or the ileum by measuring from the Ligament of Treitz.

For example, a study of three patients with height of 5'10" revealed the following measurements of the duodenum:

Pylorus—1.5 cm diameter;
Duodenal Bulb—3.4 cm length and diameter;
Duodenal Sweep—2.7 cm diameter;
Jejunum—2.7 cm diameter; and
Length of Duodenum (including bulb)—25 cm.

In this study, the measurements of one man 5'2" in height and 100 lbs are particularly interesting:

Pylorus—1.2 cm diameter;
Duodenal Bulb—2.5 cm length and diameter;
Duodenal Sweep—2.0 cm diameter;
Jejunum—2.0 cm diameter; and
Length of Duodenum (including bulb)—20 cm.

These results indicate a size relationship between the size of an individual and the measurements of his duodenum. These results point out that when designing the tubular digestive screen or the present invention for an individual, an upper gastrointestinal series will be necessary for each individual. Each tubular screen must be formed to fit the measurements of the individual, as determined by x-ray. These measurements, although not precise, are critical.

The measurements of the duodenum presented above are merely by way of example and are not intended to in any way limit the scope of the present invention.

What is claimed is:

1. A tubular digestive screen comprising a thin-walled, membrane-like tube having a top and being of a predetermined length and shaped and sized to conform to the shape and size of a stomach and intestine of an animal, further comprising:
   a firm ring at the top of the tube;
   a portion selected from the group consisting of a funnel-shaped portion and a portion which is broad and shallow below the firm ring;
   a tubular portion of tapered diameter beginning below the funnel-shaped portion; and
   a distal end of the tube comprising a brush portion comprising vertical strips extending therefrom;
   wherein the tube is held in place once inserted solely by peristaltic movements along the length of the tube.

2. A tubular digestive screen according to claim 1, wherein the tube is penetrated with small holes at the top of the tube or within the funnel-shaped portion of the tube.

3. A tubular digestive screen according to claim 1, wherein the tube is penetrated with small holes along its entire length.

4. A tubular digestive screen according to claim 1, wherein the tube is penetrated with radio-opaque dots in one vertical plane and spaced along the length of the tube.

* * * * *